(12) United States Patent
Wang

(10) Patent No.: US 10,825,556 B2
(45) Date of Patent: Nov. 3, 2020

(54) CLINICAL GRADE CONSUMER PHYSICAL ASSESSMENT SYSTEM

(71) Applicant: Welch Allyn, Inc., Skaneateles Falls, NY (US)

(72) Inventor: Ynjiun Paul Wang, Cupertino, CA (US)

(73) Assignee: Welch Allyn, Inc., Skaneateles Falls, NY (US)

(*) Notice: Subject to any disclaimer, the term of this patent is extended or adjusted under 35 U.S.C. 154(b) by 1056 days.

(21) Appl. No.: 15/006,784

(22) Filed: Jan. 26, 2016

(65) Prior Publication Data

US 2017/0212999 A1 Jul. 27, 2017

(51) Int. Cl.
*G16H 10/60* (2018.01)
*G16H 50/20* (2018.01)

(52) U.S. Cl.
CPC .......... *G16H 10/60* (2018.01); *G16H 50/20* (2018.01)

(58) Field of Classification Search
CPC ................................ G16H 50/20; G16H 10/60
See application file for complete search history.

(56) References Cited

U.S. PATENT DOCUMENTS

| | | | | |
|---|---|---|---|---|
| 5,860,740 A * | 1/1999 | Fujima | ..................... | G01J 5/02 374/126 |
| 2004/0059234 A1* | 3/2004 | Martin | ................... | A61B 5/022 600/500 |
| 2006/0189855 A1* | 8/2006 | Moriya | ............... | A61B 5/02433 600/301 |
| 2010/0179438 A1* | 7/2010 | Heneghan | ............... | A61B 5/113 600/484 |
| 2011/0190594 A1* | 8/2011 | Heit | ....................... | A61M 21/00 600/301 |
| 2012/0249956 A1* | 10/2012 | Narasimha-Iyer | ...... | A61B 3/102 351/206 |
| 2013/0046151 A1* | 2/2013 | Bsoul | .................... | A61B 5/4815 600/301 |
| 2014/0275854 A1* | 9/2014 | Venkatraman | ......... | A61B 5/681 600/301 |
| 2015/0127595 A1* | 5/2015 | Hawkins, II | ........... | G06N 7/005 706/46 |
| 2015/0359481 A1* | 12/2015 | Nyschick | .............. | A61B 5/0077 600/301 |
| 2015/0366518 A1* | 12/2015 | Sampson | .............. | A61B 5/7264 600/301 |

FOREIGN PATENT DOCUMENTS

WO WO-2005001740 A2 * 1/2005 ........... G06T 7/0012

OTHER PUBLICATIONS

Fu, Yajing, "Disease Diagnosis Supported by Hierarchical Temporal Memory," UIC-ATC-ScalCom-CBDCom-IoP 2015 (Year: 2015).*

(Continued)

*Primary Examiner* — John P Go
(74) *Attorney, Agent, or Firm* — Merchant & Gould P.C.

(57) ABSTRACT

A clinical grade consumer physical assessment system generates clinical grade physical assessment information for a patient based on a plurality of consumer grade measurements taken from different body portions of the patient using a consumer device. The system operates to correlate the plurality of consumer grade measurements, which have low resolution and accuracy, to a clinical grade result that is adequate for clinical purposes.

20 Claims, 8 Drawing Sheets

(56) References Cited

OTHER PUBLICATIONS

Scranton Gillette Communications, "Corventis Launches AVIVO Mobile Patient Management System," http://www.dicardiology.com/product/corventis-launches-avivo-mobile-patient-management-system, Apr. 22, 2009, 12 pages.

Fitbit, Inc., Fitbit Surge Fitness Super Watch, "Train smarter. Go farther." https://www.fitbit.com/surge, 2016, 14 pages.

Ryan Hurd, Dream Studies Portal, "8 Best Sleep Tracking Apps and Devices Now that Zeo is Gone," http://dreamstudies.org/2013/07/16/best-sleep-tracking-apps-devices/, Jul. 16, 2013, 12 pages.

iShoe: The Balance Company, "When it comes to health, a person's balance is the magic mirror that cannot lie." http://www.ishoebalance.com/, 2016, 3 pages.

"Scanadu Scout: A scanner packed with sensors designed to read your vital signs and send them wirelessly to your smartphone in a few seconds, any time, anywhere." https://www.indiegogo.com/projects/scanadu-scout#/, 2016, 12 pages.

Apple Inc., Apple Watch, "Track your health. Start with your heart." http://www.apple.com/watch/health/, 2016, 8 pages.

* cited by examiner

CLINICAL GRADE CONSUMER PHYSICAL ASSESSMENT SYSTEM

BACKGROUND

Telemedicine is an example of decentralized healthcare practice, using telecommunication and information technologies for providing clinical healthcare at a distance. Telemedicine helps eliminating distance barriers and improve access to medical services. Many of primary care physician consultations can be done online from a distant location. However, telemedicine or virtual medical treatment has several downsides. For example, telemedicine may actually decrease time efficiency due to the difficulties of assessing and treating patients through virtual interactions. Further, it is more difficult to obtain quality measurements, records, and clinical information without human interaction between medical professionals and patients. Poor quality of transmitted records, such as physiological measurements and patient progress reports, and decreased access to relevant clinical information can compromise the quality and continuity of patient care and increase a risk of error in delivering medical services.

To provide quality healthcare services, several clinical grade physical assessment devices can be used for accurate online diagnosis by a physician who is remotely located from a patient. These devices can be used by patients following instructions from physicians, or can be controlled remotely by the physicians. Such devices include digital stethoscope, thermometer, and cuff-less blood pressure monitor, and other tools, which are clinically approved or certified. However, one of the barriers to popular use of such devices is to have patients engage the devices. Patients can be less skilled to properly manipulate the devices than medical practitioners, or can be simply ignorant of using the devices as instructed for various reasons.

On the other hand, various devices for tracking activities, fitness, and vitals have become popular. Some tracking devices are wearable technology devices. Consumers can easily wear such devices and conveniently operate them. The tracking devices can monitor, for example, user activities, vitals, quality of sleep, fitness-related metrics (e.g., distance walked or run), calorie consumption, heartbeat, and other information. The data obtained by the consumer tracking devices can be used as accountability and motivation for personal fitness and healthy lifestyle. However, the data from the tracking devices are not clinically accurate to be used for clinical diagnosis or assessment.

SUMMARY

In general terms, this disclosure is directed to a system for providing clinical grade consumer physical assessment. In one possible configuration and by non-limiting example, the system operates to generate a clinical grade measurement based on a plurality of consumer grade measurements using a consumer device. Various aspects are described in this disclosure, which include, but are not limited to, the following aspects.

One aspect is a method for providing a clinical grade measurement. The method includes: obtaining a first measurement associated with a body of a subject using a first sensing device, the first sensing device mounted to at least one subject computing device operable by the subject, and the first sensing device arranged to measure the first measurement at a first location of the subject; obtaining a second measurement associated with the body of the subject using a second sensing device, the second sensing device mounted to the at least one subject computing device operable by the subject, and the second sensing device arranged to measure the second measurement at a second location of the subject, wherein the second location is different from the first location; and correlating, using at least one computing device, a combination of the first and second measurements to a third measurement, the third measurement representative of a physical assessment measurement of the subject and adapted for medical diagnosis of the subject.

Another aspect is an apparatus for obtaining a plurality of physical assessment measurements of a subject. The apparatus includes a housing including a consumer electronics device configured to perform one or more consumer level functionalities; a coupling device configured to secure the housing to a subject; a first sensing device mounted to the housing at a first housing location and configured to be arranged at a first subject location of the subject when the housing is secured to the subject, the first sensing device configured to monitor a first physical assessment measurement of the subject at the first subject location; and a second sensing device mounted to the housing at a second housing location and configured to be arranged at a second subject location of the subject when the housing is secured to the subject, the second sensing device configured to monitor a second physical assessment measurement of the subject at the second subject location.

Yet another aspect is a method for automatically providing a clinical grade measurement. The method includes: obtaining a plurality of physical assessment signals associated with a subject using a plurality of sensing devices, the plurality of sensing devices included in at least one subject computing device operable by the subject, and the plurality of sensing devices arranged at different locations of the at least one subject computing device; obtaining a user feedback using the at least one subject computing device, the user feedback including information associated with the subject; correlating the plurality of physical assessment signals to an output signal, the output signal representative of a physical assessment measurement of the subject and adapted for medical diagnosis of the subject; and generating a personalized diagnostic result from the output signal, the personalized diagnostic result including information personalized for the subject based on the user feedback.

DETAILED DESCRIPTION

Figure 1:
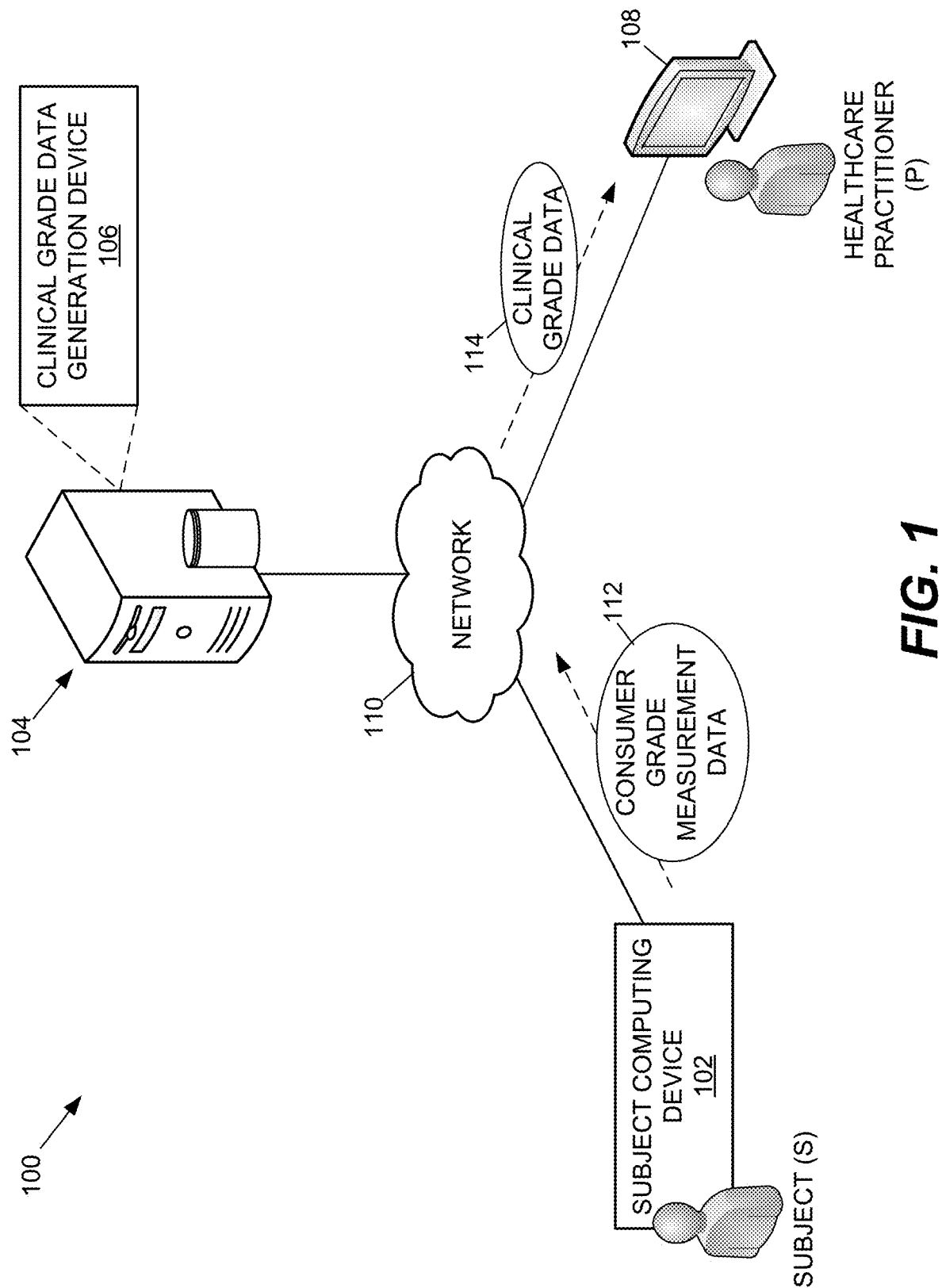
FIG. 1 schematically illustrates a clinical grade consumer physical assessment system in accordance with an exemplary embodiment of the present disclosure.

Various embodiments will be described in detail with reference to the drawings, wherein like reference numerals represent like parts and assemblies throughout the several views.

In general, a system in accordance with an example embodiment of the present disclosure operates to generate clinical grade physical assessment for a patient based on a plurality of consumer grade measurements obtained from different body portions of the patient using a consumer device. In certain examples, the system of the present disclosure includes an online machine learning device that can correlate the plurality of consumer grade measurements, which have low resolution and accuracy, to a clinical grade result that is adequate for clinical purposes.

The system of the present disclosure incorporates a plurality of sensing devices into the consumer device operable by a patient to monitor different pieces of physical assessment information (e.g., vital signs and physiological signals) from the patient. The system can then synthesize the obtained signals and generates a clinical grade signal that can be used for accurate clinical diagnosis. The consumer device is conveniently wearable by the patient without interfering with the patient's lifestyle. Examples of the consumer device include smartwatches, smartphones, and tablets. The sensing devices are ergonomically arranged in the consumer device so that the patient can easily place the sensing devices on predetermined body portions and properly obtain the measurements associated with the body portions.

The system of the present disclosure further operates to receive the patient's feedback associated with the consumer grade measurements, and generate a personalized diagnostic result based on the patient's feedback as well as the consumer grade measurements.

According to the system of the present pressure, a clinical grade patient measurement can be efficiently obtained by simply using consumer grade sensing devices integrated with a consumer device. As the consumer device is routinely used by the patient for daily purposes, necessary measurements can be easily collected without requiring the patient's significant involvement.

FIG. 1 schematically illustrates a clinical grade consumer physical assessment system 100 in accordance with an exemplary embodiment of the present disclosure. The system 100 includes a subject computing device 102, a data management system 104 including a clinical grade data generation device 106, and a healthcare practitioner computing device 108. Some embodiments of the system 100 can operate with a data communication network 110.

The subject computing device 102 is used and operated by a subject S, which is also referred to herein as a patient or consumer. As described herein, the subject computing device 102 operates to measure the subject's health condition and generate consumer grade measurement data 112. As described below, the measurement data 112 include a plurality of measurements obtained by the subject computing device 102. In some embodiments, the subject computing device 102 can transmit the measurement data 112 to the clinical grade data generation device 106 through the network 110. An example of the subject computing device 102 is described in more detail with reference to FIG. 2.

Figure 4:
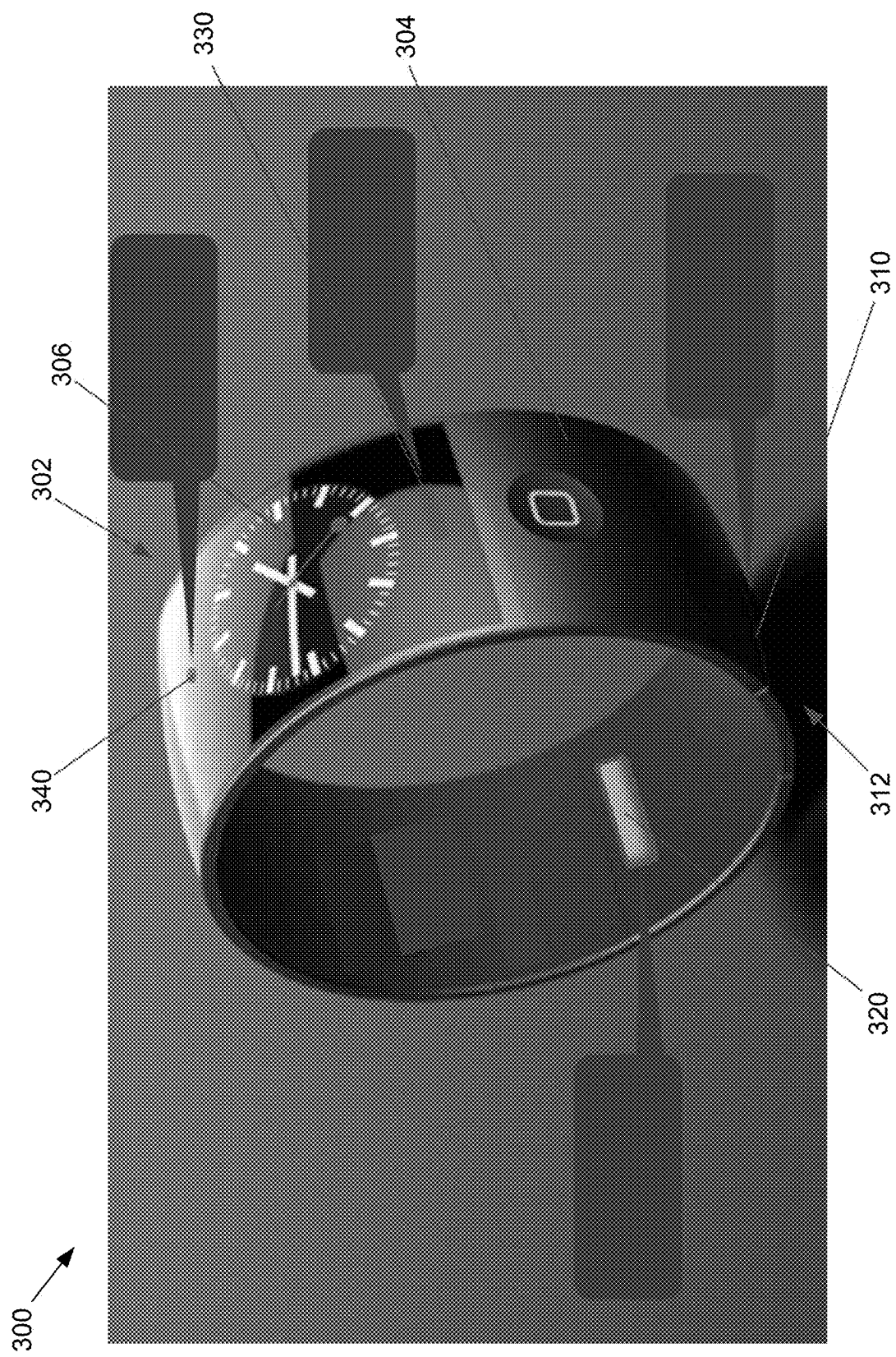
FIG. 4 is a schematic perspective view of an example subject computing device of FIG. 1.

Some examples of the subject computing device 102 are configured to be conveniently carried or worn by the subject S. The subject computing device 102 can be a consumer mobile device, which can be daily used by the subject S. For example, the subject computing device 102 is configured as a computerized wristwatch, wristband, or clip-on, as illustrated in FIG. 4. In other examples, the subject computing device 102 includes a mobile phone, a table computer, an internet enabled gaming system, an internet enabled portable television, and other portable computing devices. Since the subject computing device 102 is originally configured as a consumer device for daily purposes, the subject computing device 102 can be used to obtain a plurality of measurements (i.e., the consumer grade measurement data 112) without interfering the subject's lifestyle.

The data management system 104 operates to monitor the subject's health conditions and other information associated with the subject S. In some embodiments, the data management system 104 is operated by the healthcare practitioner P. Some embodiments of the data management system 104 are configured to receive the consumer grade measurement data 112 (and other data associated with the subject S) from the subject computing device 102, and analyze the data 112 for various purposes.

In some embodiments, the clinical grade data generation device 106 of the data management system 104 operates to generate clinical grade data 114 based on the consumer grade measurement data 112. Although it is described in this document that the clinical grade data generation device 106 is included in the data management system 104, it is possible that the clinical grade data generation device 106 is included in the subject computing device 102. An example of the clinical grade data generation device 106 is described with reference to FIGS. 6-8.

The healthcare practitioner computing device 108 is operated by the healthcare practitioner P. The healthcare practitioner P is a person, entity, institution, or agency that provides healthcare service to the subject S. Examples of healthcare practitioners P include primary care providers (e.g., doctors, nurse practitioners, and physician assistants), nursing care providers (e.g., nurses), specialty care providers (e.g., professionals in various specialties), and health professionals or institutions that provide preventive, curative, promotional and rehabilitative health care services.

In some embodiments, the healthcare practitioner P can use the healthcare practitioner computing device 108 to remotely see the subject S and provide clinical healthcare service to the subject S at a distance. The healthcare practitioner computing device 108 can receive the clinical grade data 114 from the clinical grade data generation device 106 through the network 110 and present the clinical grade data 114 to the healthcare practitioner P in various manners. Some embodiments of the healthcare practitioner computing device 108 are configured to communicate with the subject computing device 102 through the network 110 to receive and/or transmit data (e.g., the consumer grade measurement data 112). The healthcare practitioner P can transmit various pieces information, such as instructions, medications, prescriptions, and health-related suggestions (e.g., dietary treatments, suggestions, or plans), and exercise plans, to the subject computing device 102 so that the subject S receives such information on the subject computing device 102. In other embodiments, the healthcare practitioner computing device 108 can be used to control the subject computing device 102 for monitoring the subject's health conditions and obtaining various measurements through the subject computing device 102.

The data communication network 110 communicates digital data between one or more computing devices, such as among the subject computing device 102, the data management system 104, and/or the healthcare practitioner computing device 108. Examples of the network 110 include a local area network and a wide area network, such as the Internet.

In some embodiments, the network 110 includes a wireless communication system, a wired communication system, or a combination of wireless and wired communication systems. A wired communication system can transmit data using electrical or optical signals in various possible embodiments. Wireless communication systems typically transmit signals via electromagnetic waves, such as in the form of optical signals or radio frequency (RF) signals. A wireless communication system typically includes an optical or RF transmitter for transmitting optical or RF signals, and an optical or RF receiver for receiving optical or RF signals. Examples of wireless communication systems include Wi-Fi communication devices (such as utilizing wireless routers or wireless access points), cellular communication devices (such as utilizing one or more cellular base stations), and other wireless communication devices.

The consumer grade measurement data 112 includes a plurality of measurements obtained by the subject computing device 102. Such measurements include consumer grade information associated with the subject S. As described below, the subject computing device 102 includes a plurality of consumer grade sensing devices for measuring different types of physical assessment information (e.g., vital signs, physiological measurements, and biological measurements) from different portions of the subject's body.

The clinical grade data 114 includes one or more clinical grade measurements, data, and information adapted for clinical diagnosis and treatment of the subject S.

In this document, clinical grade measurement, data, or information includes information that is accurate for clinical purposes. Clinical grade information can be clinically used by healthcare practitioners to diagnose and treat patients with reasonable assurance of safety and effectiveness. Clinical grade information is typically generated by medical devices that are approved by one or more healthcare-related government bodies or authorities, such as the United States Food and Drug Administration (the FDA). For example, the FDA evaluates the risks of inaccurate or incomplete medical device data, which can lead to incorrect patient diagnosis or treatment, based on rules and regulations relevant to medical devices used for patient care.

Consumer grade measurement, data, or information includes information that is inadequate for clinical purposes. Consumer grade data is not as accurate as clinical grade and does not lead to accurate and complete diagnosis and treatment of patients. Consumer grade data are generated by consumer devices, which do not need an approval or certification by the healthcare-related government bodies or authorities. Consumer grade devices include mobile computing devices that are marketed to individuals, not businesses. For examples, the iPhone, iPad, Android smartphones and tablets, fitness tracking devices, and Internet-capable gaming devices are considered to be consumer grade devices or consumer devices. The measurements obtained using such consumer grade devices are less accurate than the measurements obtained using clinical grade devices, and do not provide clinically accurate information adapted for medical diagnosis and treatment.

In some examples, physical assessment includes examination of various aspects of a patient's health status utilizing knowledge, skills, and tools. Physical assessment information is information about the subject's health including physiological, psychological, sociocultural, and spiritual aspects. Such physical assessment can be performed by physical examination using tools and techniques. The physical examination can include inspection (visual inspection of the body), palpation (examination using the sense of touch), percussion (method by which the body is struck indirectly to elicit sounds), and auscultation (listening to sounds in body). As such, physical assessment information can include physiological and biological information based on various physical measurements and vital signs.

Vital signs are measurements of the body's basic functions and useful in detecting or monitoring medical problems. Examples of vital signs include body temperature, pulse rate (i.e., heart rate), respiration rate (i.e., breathing rate), and blood pressure. Body temperature can be taken in various manners, such as orally, rectally, by ear, or by skin. The pulse rate is a measurement of the heart rate, or the number of times the heart beats per minute. The pulse rate can also indicate a heart rhythm and the strength of the pulse. The pulse can be taken on different body portions where the arteries are located, such as on the side of the neck, on the side of the elbow, or at the wrist. The respiration rate is the number of breaths a person takes per minute and is used to note whether the person has any difficulty breathing. Blood pressure is the force of the pushing against the artery walls. There may be other vital signs, such as pain, Glasgow coma scale, pulse oximetry, blood glucose level, end-tidal $CO_2$, functional status, shortness of breath, and gait speed.

Figure 2:
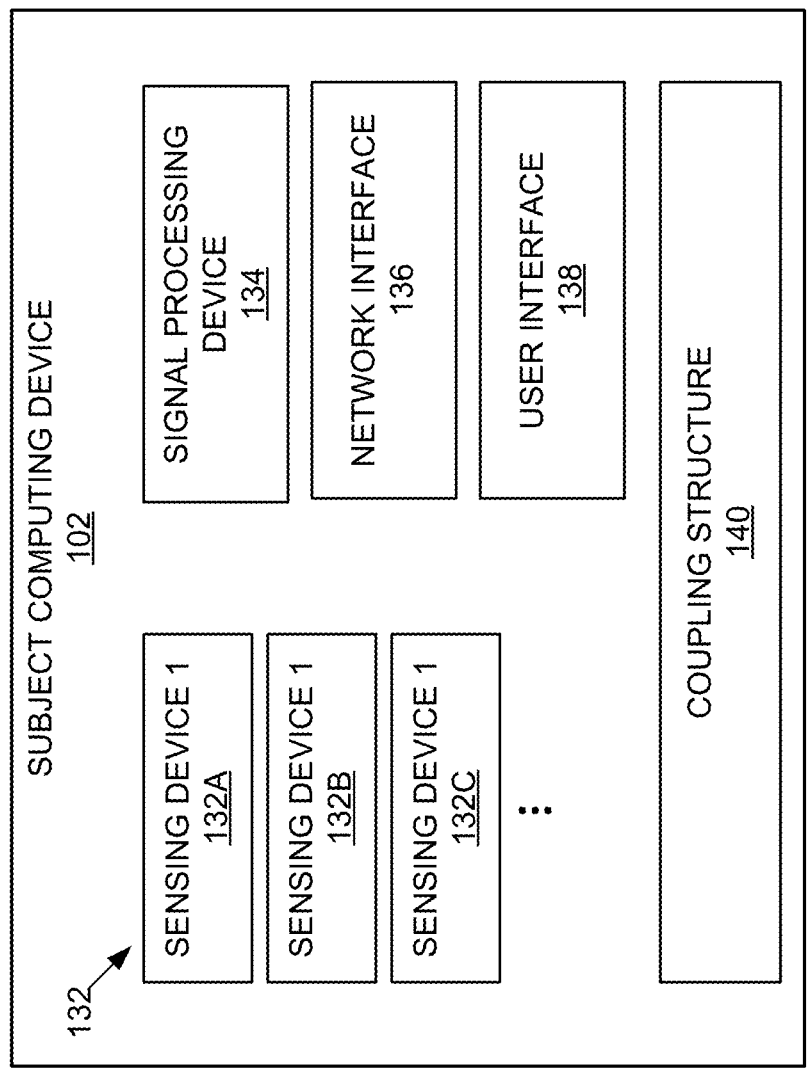
FIG. 2 schematically illustrates a subject computing device of the system of FIG. 1.

FIG. 2 schematically illustrates an example of the subject computing device 102. The subject computing device 102 includes a plurality of sensing devices 132 (including 132A, 132C, 132C, etc.), a signal processing device 134, a network interface 136, a user interface 138, and a coupling structure 140.

In some embodiments, the subject computing device 102 is configured as a wearable technology device, such as a smartwatch (as illustrated in FIG. 4). In other embodiments, the subject computing device 102 is configured as a handheld mobile device, such as a smartphone, tablet, or PDA. Although the subject computing device 102 of the present disclosure is primarily described for the purpose of healthcare services, it should be understood that the subject computing device 102 is configured to be used for other typical purposes, such as cell phone, personal digital assistant, media player, GPS navigation, access to the Internet, running third-party applications, cameras, etc.

The sensing devices 132 operate to monitor various physical assessment measurements of the subject S. In some examples, the sensing devices 132 include consumer grade sensors originally integrated with the subject computing device 102, such as an digital image capturing unit (e.g., a camera), a temperature sensing unit (e.g., thermometer), and a sound detecting unit (e.g., microphone).

The signal processing device 134 operates to process the signals obtained by the sensing devices 132. In some examples, the signal processing device 134 receives the signals from the sensing devices 132 and generates the consumer grade measurement data 112.

The network interface 136 is an interface that operates to communicate with other computing devices through the network 110. In some embodiments, the network interface 136 is configured similarly to a wireless network interface 246 as described in FIG. 3.

The coupling structure 140 is configured to couple the subject computing device 102 to a portion of the subject S.

Where the subject computing device 102 includes a wristwatch as illustrated in FIG. 4, the coupling structure 140 can include a wrist strap for holding the subject computing device 102 around the wrist of the subject S. Other types of the coupling structure 140 are also possible in other embodiments.

Figure 3:
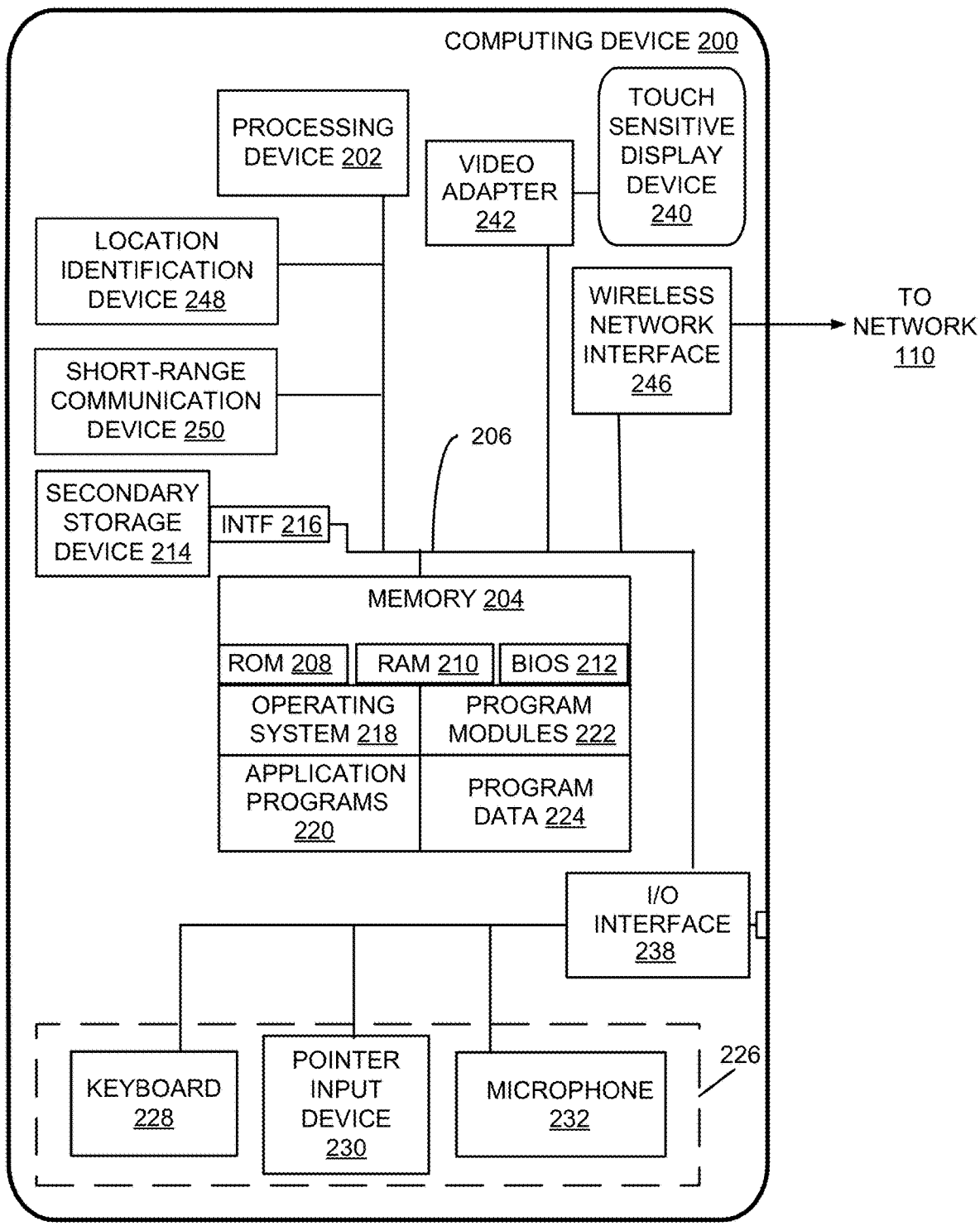
FIG. 3 illustrates an exemplary architecture of a computing device that can be used to implement aspects of the present disclosure.

FIG. 3 illustrates an exemplary architecture of a computing device that can be used to implement aspects of the present disclosure, including the subject computing device 102, the data management system 104, and the healthcare practitioner computing device 108, and will be referred to herein as the computing device 200. The computing device 200 is used to execute the operating system, application programs, and software modules (including the software engines) described herein.

The computing device 200 includes, in some embodiments, at least one processing device 202, such as a central processing unit (CPU). A variety of processing devices are available from a variety of manufacturers, for example, Intel or Advanced Micro Devices. In this example, the computing device 200 also includes a system memory 204, and a system bus 206 that couples various system components including the system memory 204 to the processing device 202. The system bus 206 is one of any number of types of bus structures including a memory bus, or memory controller; a peripheral bus; and a local bus using any of a variety of bus architectures.

Examples of computing devices suitable for the computing device 200 include a desktop computer, a laptop computer, a tablet computer, a mobile device (such as a smart phone, an iPod® mobile digital device, or other mobile devices), internet enabled television, internet enabled gaming system, or other devices configured to process digital instructions.

The system memory 204 includes read only memory 208 and random access memory 210. A basic input/output system 212 containing the basic routines that act to transfer information within computing device 200, such as during start up, is typically stored in the read only memory 208.

The computing device 200 also includes a secondary storage device 214 in some embodiments, such as a hard disk drive, for storing digital data. The secondary storage device 214 is connected to the system bus 206 by a secondary storage interface 216. The secondary storage devices and their associated computer readable media provide nonvolatile storage of computer readable instructions (including application programs and program modules), data structures, and other data for the computing device 200.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media.

A number of program modules can be stored in secondary storage device 214 or memory 204, including an operating system 218, one or more application programs 220, other program modules 222, and program data 224.

In some embodiments, computing device 200 includes input devices to enable a user to provide inputs to the computing device 200. Examples of input devices 226 include a keyboard 228, pointer input device 230, microphone 232, and touch sensitive display 240. Other embodiments include other input devices 226. The input devices are often connected to the processing device 202 through an input/output interface 238 that is coupled to the system bus 206. These input devices 226 can be connected by any number of input/output interfaces, such as a parallel port, serial port, game port, or a universal serial bus. Wireless communication between input devices and interface 238 is possible as well, and includes infrared, BLUETOOTH® wireless technology, 802.11a/b/g/n, cellular, or other radio frequency communication systems in some possible embodiments.

In this example embodiment, a touch sensitive display device 240 is also connected to the system bus 206 via an interface, such as a video adapter 242. The touch sensitive display device 240 includes touch sensors for receiving input from a user when the user touches the display. Such sensors can be capacitive sensors, pressure sensors, or other touch sensors. The sensors not only detect contact with the display, but also the location of the contact and movement of the contact over time. For example, a user can move a finger or stylus across the screen to provide written inputs. The written inputs are evaluated and, in some embodiments, converted into text inputs.

In addition to the display device 240, the computing device 200 can include various other peripheral devices (not shown), such as speakers or a printer.

When used in a local area networking environment or a wide area networking environment (such as the Internet), the computing device 200 is typically connected to the network through a network interface, such as a wireless network interface 246. Other possible embodiments use other communication devices. For example, some embodiments of the computing device 200 include an Ethernet network interface, or a modem for communicating across the network.

The computing device 200 typically includes at least some form of computer-readable media. Computer readable media includes any available media that can be accessed by the computing device 200. By way of example, computer-readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 200.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

Referring again to FIG. 3, the computing device 200 can include a location identification device 248. The location identification device 248 is configured to identify the location or geolocation of the computing device 200. The location identification device 248 can use various types of geolocating or positioning systems, such as network-based systems, handset-based systems, SIM-based systems, Wi-Fi positioning systems, and hybrid positioning systems. Network-based systems utilize service provider's network infrastructure, such as cell tower triangulation. Handset-based systems typically use the Global Positioning System (GPS). Wi-Fi positioning systems can be used when GPS is inadequate due to various causes including multipath and signal blockage indoors. Hybrid positioning systems use a combination of network-based and handset-based technologies for location determination, such as Assisted GPS.

Referring again to FIG. 3, the computing device 200 further includes a short-range wireless communication device 250. The short-range wireless communication device 250 is configured to establish short-range wireless communication with adjacent computing devices. For example, the short range wireless communication device 250 can be used to establish short-range wireless communication between the subject computing device 102 and one or more other computing devices used by the subject S. Short-range wireless communication is one-way or two-way short-range to medium-range wireless communication. Short-range wireless communication can be established according to various technologies and protocols. Examples of short-range wireless communication include a radio frequency identification (RFID), a near field communication (NFC), a Bluetooth technology, and a Wi-Fi technology.

FIG. 4 is a schematic perspective view of an example of the subject computing device 102. In the illustrated example, the subject computing device 102 is configured as a computerized wristwatch 300, which is also referred to herein as a smartwatch.

The smartwatch 300 includes a case or housing 302 and a wrist strap or band 304 (which corresponds to the coupling structure 140 as described in FIG. 2). The case 302 is configured to house mechanical and electrical components that implement typical consumer level functionalities, such as digital clock, running mobile applications, and data communication with other computing devices. Such mechanical and electrical components can be implemented as described in FIGS. 2 and 3. The smartwatch 300 includes a display screen 306, which can be touch-sensitive, on the case 302. The wrist band 304 extends from opposite ends of the case 302 to secure the smartwatch 300 to the wrist.

The smartwatch 300 is configured and used for obtaining a plurality of physical assessment measurements associated with the subject S who is using or wearing the smartwatch 300. The smartwatch 300 includes a plurality of sensing devices, which correspond to the sensing devices 132 in FIG. 2. The sensing devices are arranged at particular locations of the smartwatch 300 to perform different functions. Some examples of the sensing devices of the smartwatch 300 include a digital image capturing device, a temperature measuring device, a sound detecting device, and an optical measuring device. The configurations and operations of such sensing devices are described below. In some examples, the smartwatch 300 can be connected to, and used with, one or more other computing devices, such as a smartphone or tablet, to perform the following functions. In other examples, the smartwatch 300 can be configured to independently implement the functionalities.

In some examples, the smartwatch 300 includes a sound sensing device 310, which converts sound into an electric signal. Examples of the sound sensing device 310 include a microphone of various types. The sound sensing device 310 can be used to provide digital stethoscope functionality. However, the sound sensing device 310 need not be a clinical grade stethoscope. For example, a consumer grade microphone integrated in a typical smartwatch can be used without modification.

The sound sensing device 310 is placed at a location of the smartwatch 300 that enables the subject S to conveniently place the sound sensing device 310 against the chest for auscultation. In some examples, the sound sensing device 310 can be arranged at a bottom portion 312 of the wrist band 304, which is generally opposite to the case 302. In this configuration, the subject S wearing the smartwatch 300 can ergonomically place the bottom portion 312 of the smartwatch 300 against the chest by bending the subject's forearm toward the chest without twisting the forearm or wrist. In other examples, the sound sensing device 310 can be arranged at different locations of the smartwatch 300.

When the sound sensing device 310 becomes in contact with, or adjacent to, the subject's chest, the sound sensing device 310 detects internal sounds (e.g., sounds from lung, heart, intestines, and/or blood flow in arteries and veins) from the subject's body. In some examples, the detected acoustic sound wave can be converted into an electrical sound signal by the signal processing device 134 (FIG. 2). The signal processing device 134 can further process the sound signal to enhance the signal quality.

In other examples, the sound sensing device 310 is made separately from the smartwatch 300 and removably coupled or attached to the smartwatch 300. The sound sensing device 310 can also be used with other body portions than the chest for the same or different functionalities.

Referring again to FIG. 4, the smartwatch 300 can include an optical measuring device. Such an optical measuring device includes a blood pressure monitor device 320. In some examples, the blood pressure monitor device 320 is a noninvasive blood pressure monitoring device employing ballistocardiography and photoplethysmography. For example, the blood pressure monitor device 320 includes a cuff-less optical based blood pressure monitor module, which includes a LED light source and a photo-diode. The optical blood pressure monitor device can detect a pulse wave from the wrist radial artery. In other examples, other types of blood pressure monitor devices can be incorporated in the smartwatch 300.

The blood pressure monitor device 320 is arranged at a location of the smartwatch 300 that is placed at or adjacent a portion of the wrist (e.g., the wrist radial artery) for properly detecting the subject's blood pressure. In some examples, the blood pressure monitor device 320 is arranged at an inner surface of the wrist band 304 such that the blood pressure monitor device 320 is placed at the wrist radial artery of the subject S when the subject S wears the smartwatch 300. For example, a molded wrist radial artery cavity watch belt for the smartwatch 300 is designed to closely fit the LED light source and the photo-diode sensor relative to the wrist radial artery position when the subject S wears the smartwatch 300.

A pulse wave or signal detected by the blood pressure monitor device 320 can represent a blood pressure and/or heart rate. In some examples, the detected signal can be processed with filtering and phase detectors by the signal processing device 134 (FIG. 2) to generate a blood pressure signal of enhanced quality. In other examples, the detected signal can be used for subsequent processes (e.g., as described in FIGS. 6-8) without such preliminary signal processing.

With continued reference to FIG. 4, the smartwatch 300 includes a temperature sensing device 330. In some examples, the temperature sensing device 330 includes an infrared thermometer, which infers temperature from a portion of the thermal radiation emitted by the subject S being measured. In other examples, other types of thermometers can be used for the temperature sensing device 330.

The temperature sensing device 330 is positioned at a location of the smartwatch 300 that enables the subject S to easily measure the subject's body temperature. In some examples, the temperature sensing device 330 is integrated in front of the case 302. For example, the temperature sensing device 330 is arranged below the display screen 306 of the case 302. In this configuration, the subject S can easily position the temperature sensing device 330 close to the subject's forehead by moving the wrist to the subject's forehead without turning the wrist or forearm. In some examples, the subject S can bring the smartwatch 300 in contact with a portion of the subject's body such that the temperature sensing device 330 interacts with the body, while the smartwatch 300 is held to the wrist of the subject S. A signal (e.g., radiant power) detected by the temperature sensing device 330 can be converted to an electrical signal by the signal processing device 134 (FIG. 2).

Referring still to FIG. 4, the smartwatch 300 includes an image capturing device 340. In some examples, the image capturing device 340 includes a digital camera that is originally integrated with the smartwatch 300. The image capturing device 340 can be used to take pictures or videos of the subject's body portions, such as the throat, mouth, face, and other internal or external body portions.

The image capturing device 340 is ergonomically arranged such that the subject S can easily place the image capturing device 340 around a body portion to be captured. In some examples, the image capturing device 340 is arranged in front of the case 302. For example, the image capturing device 340 is positioned above the display screen 306 of the case 302. In this configuration, the subject S can easily position the image capturing device 340 close to different body portions (such as a face to take a facial image). For example, the subject S can easily place the face of the case 306 toward the subject's open mouth and take a throat video and/or image. In some examples, the smartwatch 300 further includes image capturing enhancement devices, such as lighting sources (e.g., illumination LED light sources) and automatic focusing features, which improve the quality of the images and/or videos captured by the image capturing device 340. In some examples, the image and/or video signals captured by the image capturing device 340 can be processed by the signal processing device 134 (FIG. 2).

In some examples, the signals detected by the sensing devices 310, 320, 330, and 340 are not sufficiently accurate to be used for clinical purposes. For examples, the sensing devices integrated in the smartwatch 300 are not configured as clinical grade devices for various reasons, such as technical limitations and/or cost-efficient purposes. In such cases, the signals detected using the smartwatch 300 can be transmitted to the data management system 104 for subsequent analysis. In other examples, the smartwatch 300 is configured to process the signals independently.

It is primarily described that the detected signals are obtained, processed, and managed by the smartwatch 300, which can also transmit the signals to the data management system 104. In other examples, the signals obtained by the sensing devices (including 310, 320, 330, and 340) can be transmitted to another subject computing device, such as a smartphone, which is connected to the smartwatch 300 via, for example, short-range wireless communication network (e.g., a radio frequency identification (RFID), a near field communication (NFC), a Bluetooth technology, and a Wi-Fi technology). The subject computing device receiving the signals from the smartwatch 300 can then process and/or manage the signals and transmit them to the data management system 104.

It is also understood that the subject computing device 102 can be of different types than the smartwatch 300 as illustrated in FIG. 4. For example, a smartphone or a tablet can be the subject computing device 102, including the sensing devices described above and performing the same or similar operations. In other examples, two or more computing devices 102 can be used together to implement the configurations and operations described above. For example, the smartwatch 300 can be used together with a smartphone connected to the smartwatch 300, and at least one of the sensing devices 310, 320, 330, and 340 of the smartwatch 300 described above can be included in the smartphone used by the subject S.

Figure 5:
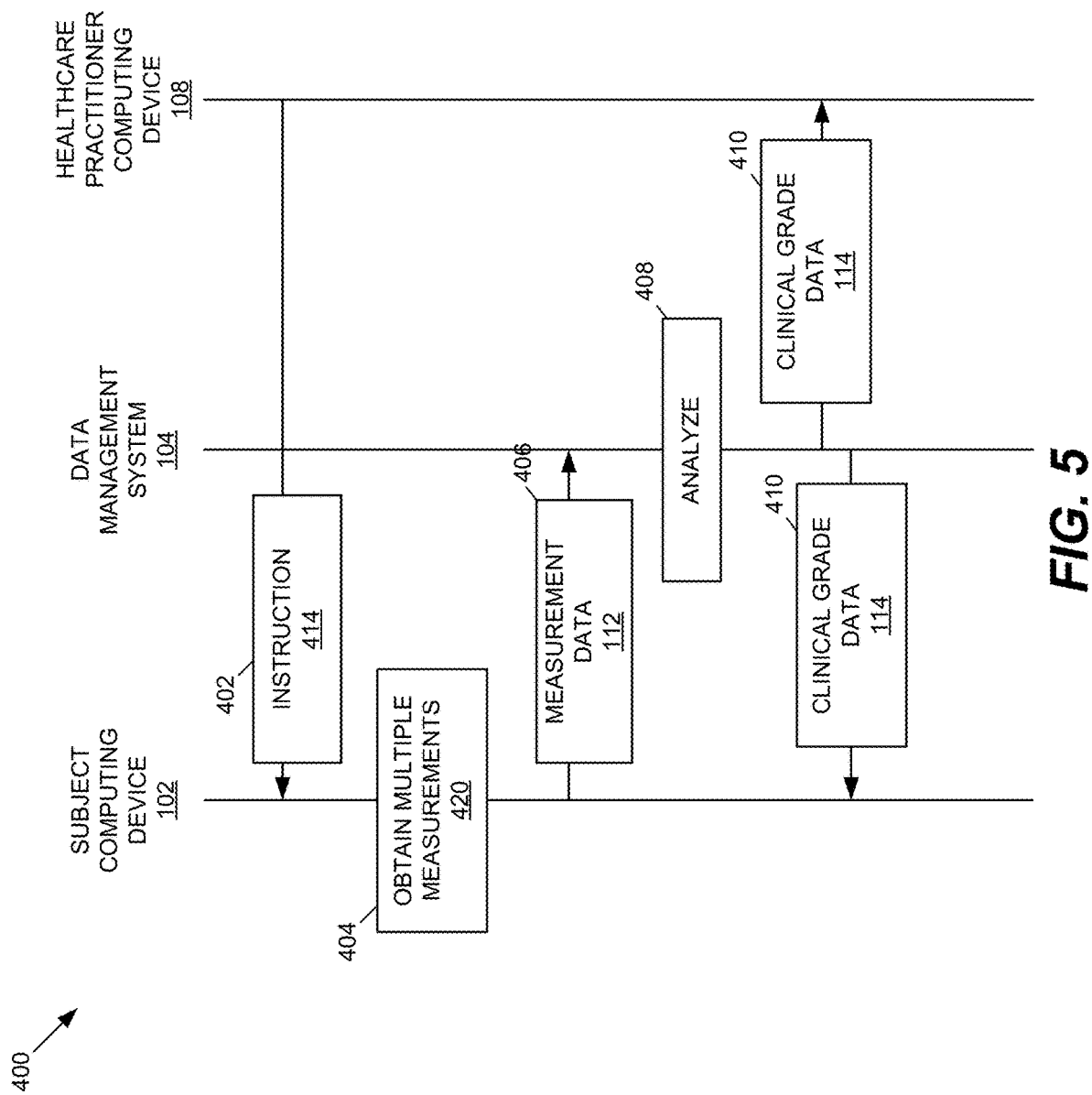
FIG. 5 is a flowchart illustrating an example method of operating the clinical grade consumer physical assessment system of FIG. 1.

FIG. 5 is a flowchart illustrating an example method 400 of operating the clinical grade consumer physical assessment system 100.

The method 400 can begin with operation 402 in which the healthcare practitioner P provides an instruction 414 to the subject S. In some examples, the healthcare practitioner P can be remotely connected to the subject S, and provide healthcare services to the subject S, using the healthcare practitioner computing device 108 and the subject computing device 102 via the network 110. During the online meeting, the healthcare practitioner P can instruct the subject S to obtain certain measurements associated with the subject S, such as internal body sounds, blood pressure, body temperature, and body images, using the subject computing device 102. In other examples, the healthcare practitioner P can directly control the subject computing device 102 to obtain such measurements with no or little the subject's involvement. In yet other examples, the subject computing device 102 is configured to automatically perform measuring physical assessment information using the integrated sensing devices. The subject computing device 102 can continuously monitor such physical assessment information of the subject S and transmit the information (i.e., the measurement data 112) to the data management system 104 and/or the healthcare practitioner computing device 108 either periodically or in real-time. Alternatively, the subject computing device 102 can be preset to detect the physical assessment information at certain intervals or at particular times.

Figure 6:
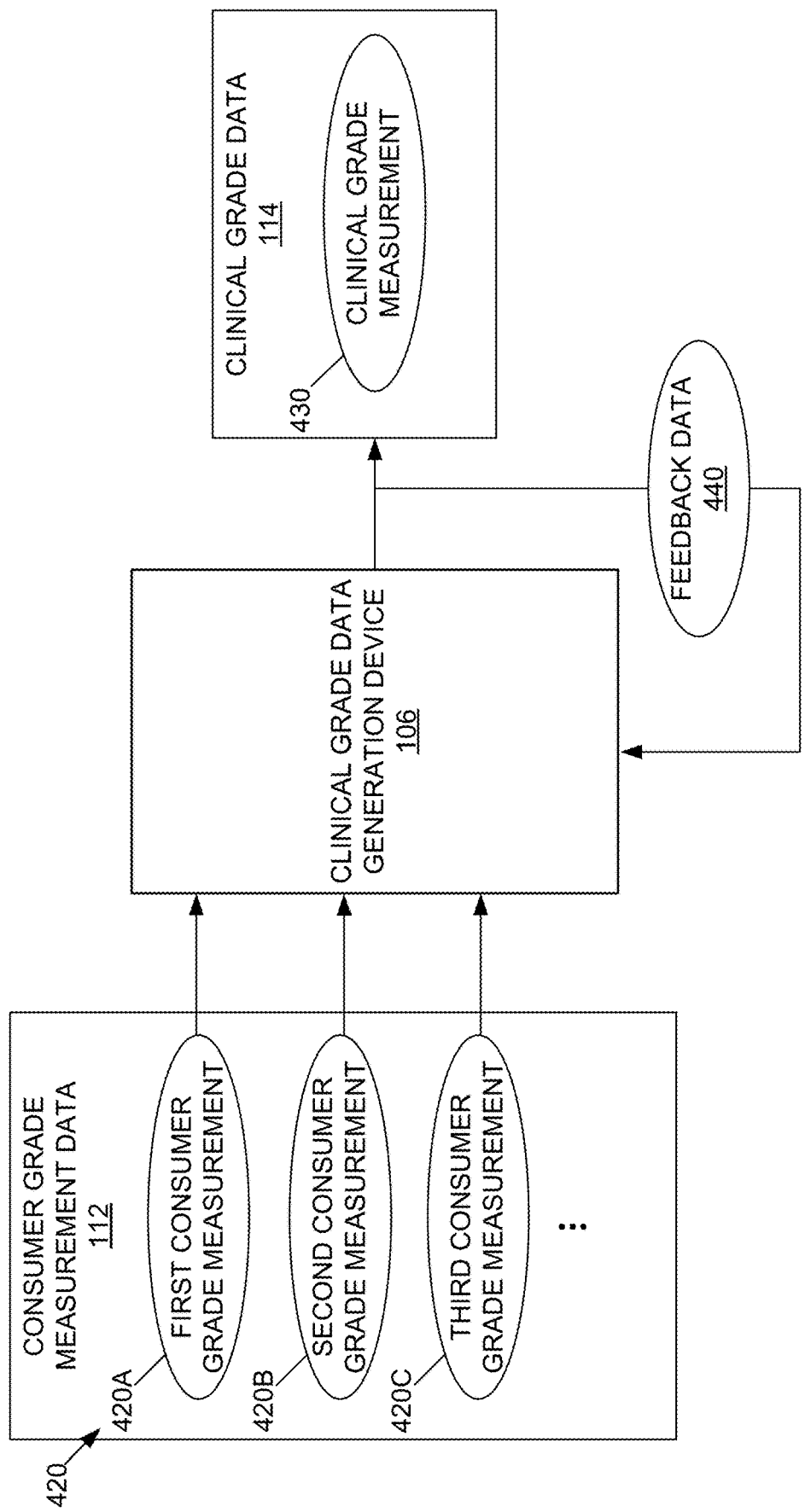
FIG. 6 schematically illustrates an example clinical grade data generation device of the system of FIG. 1.

At operation 404, the subject S uses the subject computing device 102 with different positions of the subject's body to obtain a plurality of physical assessment measurements 420 (as also shown in FIG. 6) associated with such different body portions of the subject S. In some examples, the measurements 420 include different types of physical assessment information (e.g., vital signs and physiological information). In the example of the subject computing device 102 as illustrated in FIG. 4, the measurements 420 include body sounds, blood pressure, body temperature, and body images. Example operations of the subject computing device 102 for obtaining the measurements are described above with reference to FIG. 4.

At operation 406, the subject computing device 102 generates the measurement data 112 including the measurements 420 obtained at the operation 404. As described herein, at least one of the measurements 420 is consumer grade information, and thus, the measurement data 112 include consumer grade information. In this regard, the measurement data 112 is also referred to as consumer grade measurement data 112. The subject computing device 102 transmits the measurement data 112 to the data management system 104 for further analysis.

At operation 408, the data management system 104 receives the consumer grade measurement data 112 from the subject computing device 102 and analyzes the consumer grade measurement data 112. In some examples, the clinical grade data generation device 106 of the data management system 104 operates to generate the clinical grade data 114 based on the consumer grade measurement data 112. An example operation of the clinical grade data generation device 106 is described with reference to FIGS. 6-8.

At operation 410, the data management system 104 transmits the clinical grade data 114 to either or both of the subject computing device 102 and the healthcare practitioner computing device 108. The clinical grade data 114 can be presented to the subject S and/or the healthcare practitioner P. In some examples, the clinical grade data 114 is displayed on the subject computing device 102 and/or the healthcare practitioner computing device 108. The healthcare practitioner P can refer to information included in the clinical grade data 114 to provide clinical services to the subject S.

FIG. 6 schematically illustrates an example of the clinical grade data generation device 106. As described, the clinical grade data generation device 106 operates to receive the consumer grade measurement data 112 and generate the clinical grade data 114.

The measurement data 112 include information about a plurality of measurements 420 (including 420A, 420B, 420C, etc.). At least some of the measurements 420 can be of different types and obtained from different body portions of the subject S. The subject computing device 102 is a consumer grade device, and thus at least one of the measurements 420 is consumer grade information, which is inappropriate for clinical diagnosis and treatment.

The clinical grade data generation device 106 generates the clinical grade data 114 based on the plurality of measurements 420. In some examples, the clinical grade data generation device 106 operates to correlate a combination of at least some of the measurements 420 into one or more clinical grade measurements 430. The clinical grade measurements 430 provide clinical grade information about the subject's physical assessment information that is accurate for clinical diagnosis and treatment of the subject S. The clinical grade measurements 430 are included in the clinical grade data 114.

In some examples, the clinical grade data generation device 106 generates feedback data 440 adapted to improve the operation of the clinical grade data generation device 106. The feedback data 440 can include information about the correlation between the consumer grade measurement data 112 and the clinical grade data 114, and is used to improve future correlation operations. For example, when the clinical grade data generation device 106 obtains one or more measurements 420 in subsequent measuring operations, the feedback data 440 is used by the clinical grade data generation device 106 in correlating the one or more measurements 420 into a clinical grade measurement 430. The clinical grade measurement 430 generated based on the feedback data 440 can provide clinical grade information about the subject's physical assessment information that is more accurate for clinical diagnosis and treatment than the previous clinical grade measurements 430. The feedback data 440 can be generated when the clinical grade measurement 430 performs the correlation and can be used for any subsequent correlations.

Figure 7:
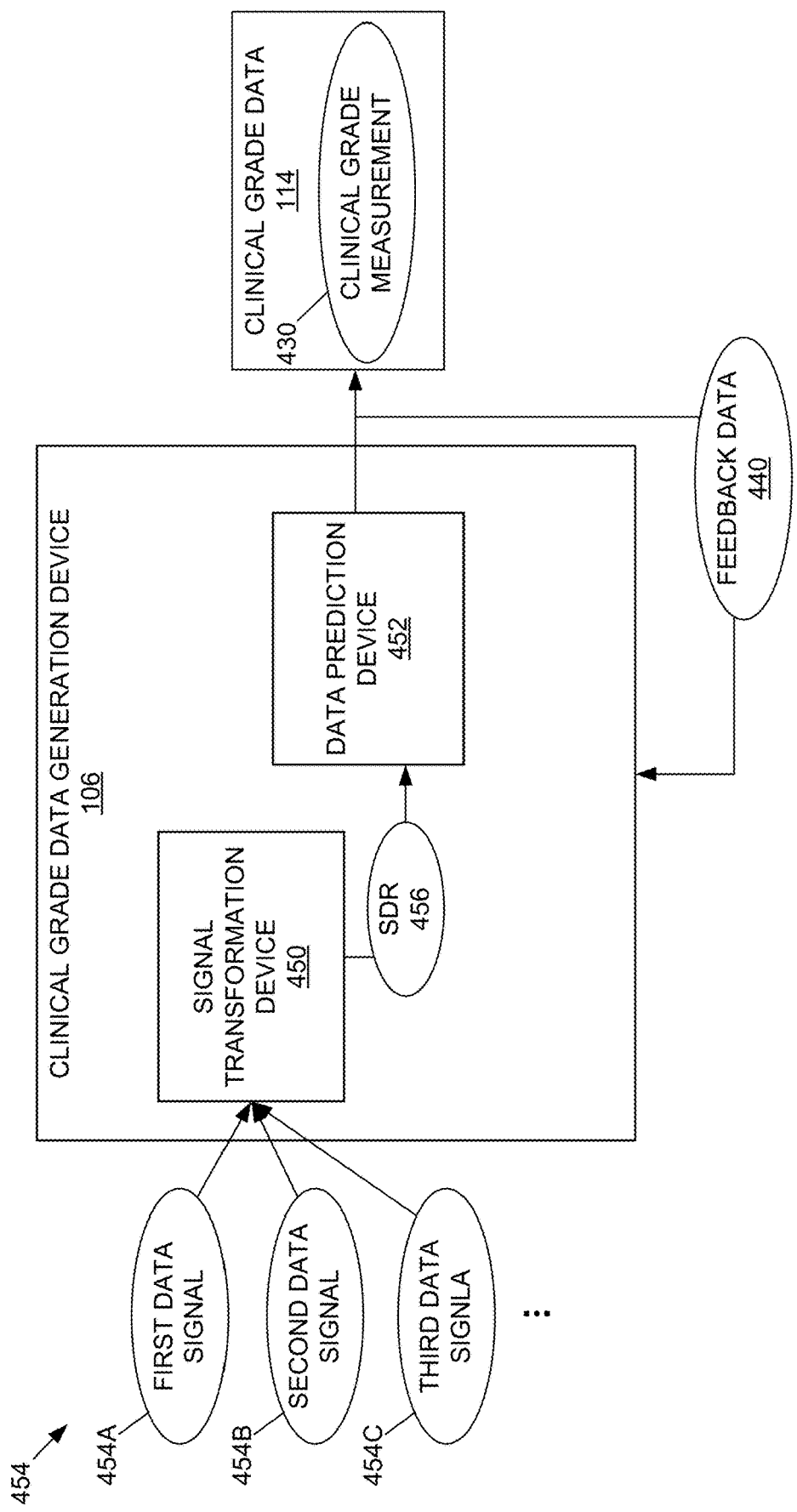
FIG. 7 schematically illustrates the clinical grade data generation device of FIG. 6.

FIG. 7 schematically illustrates an example of the clinical grade data generation device 106 of FIG. 6. The clinical grade data generation device 106 can include a signal transformation device 450 and a data prediction device 452.

In some examples, the clinical grade data generation device 106 employs a machine learning model. For example, the clinical grade data generation device 106 uses an online machine learning model, such as hierarchical temporal memory (HTM).

The signal transformation device 450 operates to map a plurality of data signals 454 (including 454A, 454B, 454C, etc.) into sparse distributed representations 456 (SDRs), which are to be used by HTM. The data signals 454 correspond to the measurements 420 obtained using the subject computing device 102 as illustrated in FIG. 6. The SDRs are binary representations of data consisting of many bits with a small percentage of the bits active (1s). For example, the SDRs can be implemented with 2048 columns and 64 k artificial neurons where as few as 40 might be active at once. The SDRs have several advantages over traditional dense representations. For example, the SDRs are tolerant of corruption and ambiguity due to the meaning of the representation being shared or distributed across a small percentage of active bits. In an SDR, a single bit does not affect the overall meaning much. Further, as the meaning of a representation is distributed across all active bits, similarity between two representations can be used as a measure of semantic similarity in the objects they represent. As such, the bits in SDRs have semantic meaning, and such meaning is distributed across the bits.

The data prediction device 452 operates to predict the clinical grade measurement 430 based on the sparse distributed representations 456 from the signal transformation device 450. The data prediction device 452 can employ hierarchical temporal memory (HTM). In some examples, the data prediction device 452 using the HTM can learn by identifying and memorizing spatial patterns of the SDRs 456 (e.g., combinations of input bits often occurring at the same time), and then identifies temporal sequences of spatial patterns that are likely to occur one after another. The data prediction device 452 operates to generate the clinical grade measurement 430 that has an accuracy rate higher than the consumer grade measurements 420. The accuracy rate of the clinical grade measurement 430 is adapted for clinical purposes, satisfying the relevant healthcare-related rules and regulations as described above.

Figure 8:
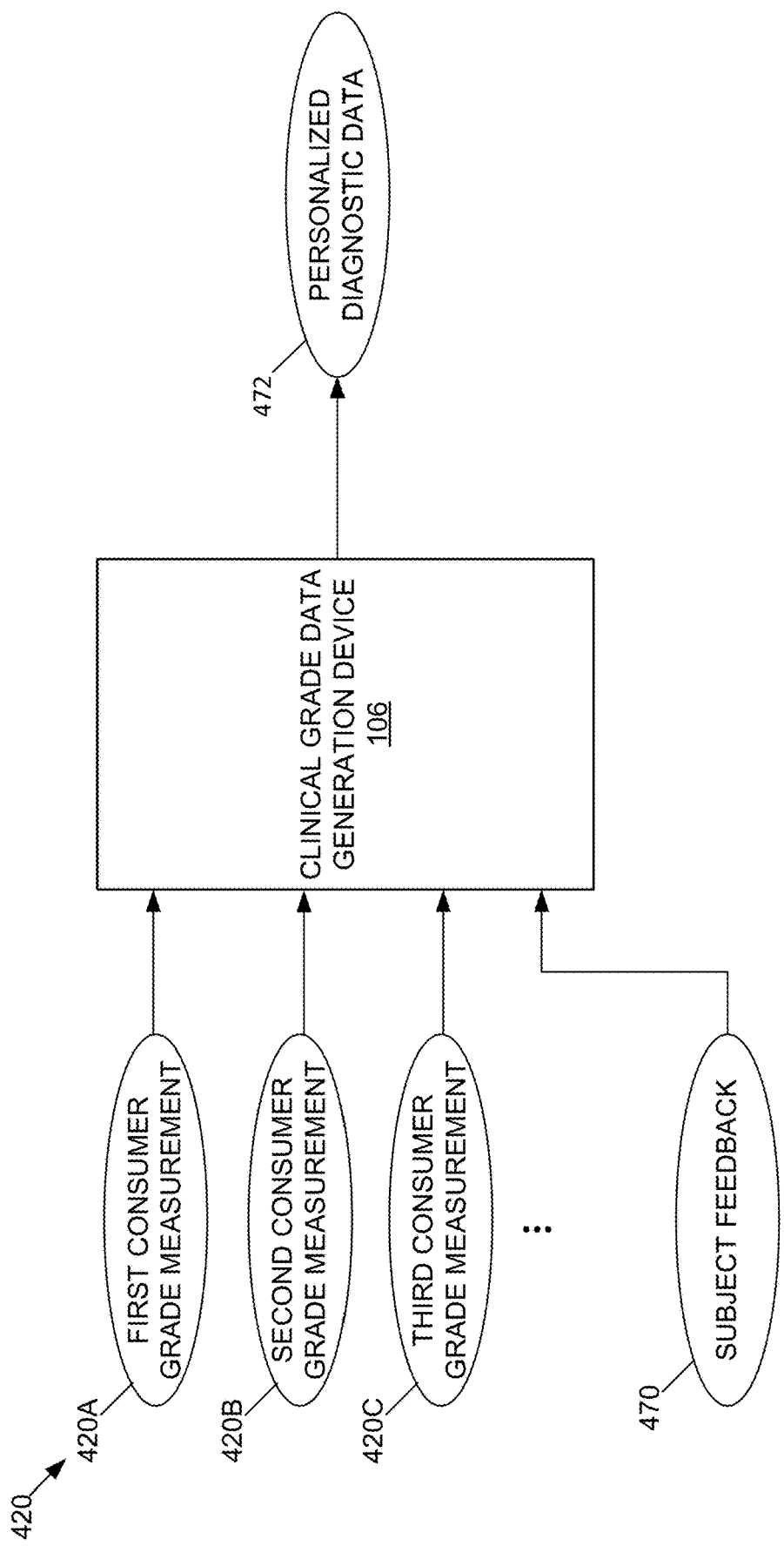
FIG. 8 schematically illustrates another example of the clinical grade data generation device of FIG. 1.

FIG. 8 schematically illustrates another example of the clinical grade data generation device 106. The clinical grade data generation device 106 of this example operates similarly to the clinical grade data generation device 106 as described in FIG. 6. Therefore, the description of the clinical grade data generation device 106 in this example is limited to the differences from the clinical grade data generation device 106 of FIG. 6.

In this example, the clinical grade data generation device 106 receives a subject feedback 470, as well as a plurality of consumer grade measurements 420, and generates a personalized diagnostic data 472. The subject computing device 102 is configured to enable the subject S to input the subject feedback 470. For example, the subject computing device 102 displays a user interface with which the subject S enters the subject feedback 470.

The subject feedback 470 includes information about the subject's personal conditions when obtaining the plurality of consumer grade measurements 420. The clinical grade data generation device 106 uses the subject feedback 470 to learn the subject's personal reactions, responses, behavior, body characteristics over time, and generate a diagnostic result personalized for the subject S.

In some examples, the subject feedback 470 includes the subject's subjective responses associated with the measurements 420. For example, the subject feedback 470 includes the subject's feeling on the subject's body conditions when the measurements 420 are obtained using the subject computing device 102. When the subject computing device 102 performs the physical assessment of the subject S using the sensing devices 132, the subject S can also provide the subject's feeling at the same time. As such, the subject feedback 470 is used to provide additional meaning for the measurement data 112 collected by the subject computing device 102. When or after collecting the measurements 420, the subject computing device 102 can ask the subject S to provide the feeling on the body condition, such as whether the subject S feels comfortable, uncomfortable, good, bad, normal, abnormal, dizzy, intense, or any other types of feeling.

The subject feedback 470 can include a variety of information (objective and/or subjective) other than the measurements 420 collected by the subject computing device 102. Examples of the subject feedback 470 include the subject's activities, the subject's status, the subject's body characteristics, the subject's judgment or perspective on the body conditions, and the subject's feeling on the body conditions.

The personalized diagnostic data 472 is generated based on the subject feedback 470 as well as the measurements 420. The personalized diagnostic data 472 includes the clinical grade data 114 (including the clinical grade measurement 430), and an interpretation of the clinical grade data 114 based on the subject feedback 470. For example, where the clinical grade data 114 includes a same blood pressure of 140/90 mmHg for two different subjects S, the subjects S can have different feelings for the same blood pressure. One subject S can feel fine with the blood pressure, and the other can feel dizzy with the same blood pressure. Thus, the clinical grade data generation device 106 refers to such different responses from the subjects and generates the personalized diagnostic data 472 that, for example have different interpretations about the conditions these subjects S.

The subject feedback 470 can include any user specific inputs, such as age, race, physical information, subjective feeling, date and times, moods, places, surroundings, and any other conditions and information that can cause different patients to have different responses to the same health-related conditions.

The various examples and teachings described above are provided by way of illustration only and should not be construed to limit the scope of the present disclosure. Those skilled in the art will readily recognize various modifications and changes that may be made without following the example examples and applications illustrated and described herein, and without departing from the true spirit and scope of the present disclosure.

What is claimed is:

1. A method for providing a clinical grade measurement, the method comprising:

obtaining a first consumer grade measurement associated with a first portion of a body of a subject using a first consumer grade sensing device, the first consumer grade sensing device mounted to at least one subject computing device operable by the subject, and the first consumer grade sensing device configured to obtain a first type of physical assessment information, wherein the first consumer grade measurement does not satisfy accuracy requirements for a medical diagnosis;

obtaining a second consumer grade measurement associated with a second portion of the body of the subject using a second consumer grade sensing device, the second consumer grade sensing device mounted to the at least one subject computing device operable by the subject, and the second consumer grade sensing device configured to obtain a second type of physical assessment information, wherein the second portion of the body is different from the first portion of the body, and the second type of physical assessment information is different from the first physical assessment information, wherein the second consumer grade measurement does not satisfy accuracy requirements for the medical diagnosis; and analyzing, using at least one computing device operating a clinical grade data generation device, a combination of the first and second measurements using a machine learning model to synthesize a third clinical grade measurement by:

mapping, with a signal transformation device, the first and second measurements into sparse distributed representations; and predicting, with a data prediction device employing hierarchical temporal memory, based on the sparse distributed representations, the third clinical grade measurement representative of a clinical grade physical assessment measurement of the subject and adapted for the medical diagnosis of the subject regarding a third physical assessment, wherein the third clinical grade measurement has an accuracy rate higher than the first and second measurements so that the accuracy rate of the third clinical grade measurement satisfies requirements for the medical diagnosis; and transmitting the third clinical grade measurement to a healthcare practitioner computing device.

2. The method of claim 1, further comprising:

receiving, at the at least one computing device, a feedback data from the subject, the feedback data including subjective information about body conditions of the subject associated with the first and second measurements; and generating personalized diagnostic data for the subject synthesized from the first second measurements combined with the feedback data.

3. The method of claim 1, further comprising:

obtaining at least one fourth consumer grade measurement associated with the body of the subject using the at least one subject computing device; and analyzing, using the at least one computing device, the at least one fourth consumer grade measurement to predict a fifth clinical grade measurement based on the feedback data, the fifth measurement representative of the clinical grade physical assessment measurement of the subject, providing clinically accurate information adapted for medical diagnosis of the subject.

4. The method of claim 1, wherein the at least one computing device includes the at least one subject computing device.

5. The method of claim 1, further comprising:
transmitting the third measurement to the at least one subject computing device to enable the at least one subject computing device to display the third measurement thereon.

6. The method of claim 1, wherein the at least one subject computing device is configured to be wearable by the subject and perform one or more consumer level functionalities.

7. The method of claim 1, wherein the at least one subject computing device includes a smartwatch.

8. The method of claim 1, further comprising:
obtaining a user feedback using the at least one subject computing device, the user feedback including information associated with the subject relevant to the clinical grade physical assessment measurement;
generating a personalized diagnostic result based on the analysis, the personalized diagnostic result including information personalized for the subject based on the user feedback.

9. The method of claim 8, wherein the user feedback includes at least one of a subject's activity, a subject's body characteristic, a subject's judgment on the subject's body condition, and a subject's feeling on the subject's body condition.

10. An apparatus for obtaining a plurality of physical assessment measurements of a subject, the apparatus comprising:
a housing including a consumer electronics device configured to perform one or more consumer level functionalities;
a coupling device configured to secure the housing to a subject;
a first consumer grade sensing device mounted to the housing at a first housing location and configured to be arranged at a first portion of a body of the subject when the housing is secured to the subject, the first consumer grade sensing device configured to monitor a first consumer grade physical assessment measurement of the subject at the first portion of the body, wherein the first consumer grade physical assessment measurement does not satisfy accuracy requirements for a medical diagnosis;
a second consumer grade sensing device mounted to the housing at a second housing location and configured to be arranged at a second portion of the body of the subject when the housing is secured to the subject, the second consumer grade sensing device configured to monitor a second consumer grade physical assessment measurement of the subject at the second portion of the body, wherein the second consumer grade physical assessment measurement does not satisfy accuracy requirements for a medical diagnosis;
a clinical grade data generation device configured to analyze the first and second consumer grade physical assessment measurements using a machine learning model by mapping the first and second consumer grade physical assessment measurements into sparse distributed representations and employing hierarchical temporal memory to predict a third measurement based on the sparse distributed representations, the third measurement representative of a clinical grade physical assessment measurement of the subject and adapted for the medical diagnosis of the subject regarding a third physical assessment, wherein the third clinical grade measurement has an accuracy rate higher than the individual first and second measurements so that the accuracy rate of the third clinical grade measurement satisfies requirements for medical diagnosis for the physical assessment and the accuracy rate of the first and second measurements do not satisfy requirements for medical diagnosis for the physical assessment; and
a network interface configured to transmit the third measurement to a healthcare practitioner computing device and receive information from the healthcare practitioner computing device.

11. The apparatus of claim 10, wherein the clinical grade data generation device generates feedback data including information representative of a result of the analysis, the feedback data being used to adjust the result of the analysis.

12. The apparatus of claim 11, wherein:
the housing includes a display panel configured to display time using the consumer electronics device;
the coupling device includes a strap portion configured to hold the apparatus to a wrist of the subject; and
the first and second consumer grade sensing devices include at least one of a digital image capturing device, a temperature measuring device, a sound detecting device, and an optical measuring device.

13. The apparatus of claim 12, wherein the digital image capturing device is arranged adjacent the display panel of the housing and configured to enable the subject to capture a facial image of the subject while the apparatus is held to the wrist of the subject.

14. The apparatus of claim 12, wherein the temperature measuring device is arranged adjacent the display panel of the housing and configured to enable the subject to bring the housing in contact with a portion of the subject's body while the apparatus is held to the wrist of the subject.

15. The apparatus of claim 14, wherein the temperature measuring device includes an infrared thermometer.

16. The apparatus of claim 12, wherein the sound detecting device includes a microphone associated with the consumer electronics device and configured to enable the subject to perform auscultation of the subject's body while the apparatus is held to the wrist of the subject.

17. The apparatus of claim 12, wherein the optical measuring device includes a noninvasive blood pressure monitoring device, the blood pressure monitoring device employing ballistocardiography and photoplethysmography.

18. The apparatus of claim 10, wherein the information comprises medications.

19. The apparatus of claim 10, wherein the network interface is further configured to receive instructions from the healthcare practitioner computing device to control the subject computing device and obtain the first and second measurements.

20. The method of claim 1, wherein the first consumer grade sensing device and the second consumer grade sensing device are not FDA approved; and the third measurement is representative of a measurement obtained by an FDA approved device.

* * * * *